United States Patent [19]

Jay

[11] 4,015,938
[45] Apr. 5, 1977

[54] SAMPLE SUPPLY APPARATUS AND METHOD FOR AUTOMATIC ANALYSIS SYSTEMS

[75] Inventor: Ronald Frank Jay, New Malden, England

[73] Assignee: Technicon Instruments Corporation, Tarrytown, N.Y.

[22] Filed: Nov. 18, 1975

[21] Appl. No.: 633,059

[52] U.S. Cl. .................... 23/230 R; 23/253 R; 23/259; 73/425.6
[51] Int. Cl.² .................. G01N 1/14; G01N 1/18
[58] Field of Search ........... 23/259, 230 R, 253 R; 73/425.4 R, 425.6

[56] References Cited
UNITED STATES PATENTS

| | | | |
|---|---|---|---|
| 3,186,235 | 6/1965 | Ferrari | 23/253 X |
| 3,241,921 | 3/1966 | Ferrari | 23/259 X |
| 3,419,358 | 12/1968 | Smythe et al. | 23/253 X |
| 3,826,615 | 7/1974 | Smythe et al. | 23/230 R |
| 3,843,326 | 10/1974 | Lichtenstenen | 23/253 X |

Primary Examiner—R.E. Serwin
Attorney, Agent, or Firm—S. P. Tedesco

[57] ABSTRACT

Method and apparatus for fluid supply for a continuous-flow analysis system which apparatus includes conduit means passing a stream segmented by an immiscible fluid, and a tube having an inlet portion movable out of and into an operative position a distance within the conduit in an upstream direction and being of a cross-sectional dimension which does not occlude the conduit.

13 Claims, 2 Drawing Figures

SAMPLE SUPPLY APPARATUS AND METHOD FOR AUTOMATIC ANALYSIS SYSTEMS

This invention relates to sample supply apparatus for automatic analysis systems.

Automatic liquid analysis systems for selectively treating and analyzing a plurality of liquid samples passed through in seriatim fashion have been disclosed, for example, in U.S. Pat. Nos. 2,797,149 and 3,241,432. In such systems, a plurality of liquid samples are introduced successively as a continuous flowing stream into an analysis apparatus, mixed with reagents and analyzed for particular constituents. The successive liquid samples in the flowing stream are separated by at least one air segment of sufficient volume to occlude the conduit along which the stream is directed. Contamination between successive liquid samples in the flowing stream is prevented or reduced by the presence of the air segments, which function to maintain the successive samples discrete and also, to scrub the residue of a previously passed sample from the interior of the conduit.

In the sample supply apparatus described in de Jong U.S. Pat. No. 3,134,263 a wash liquid segment is aspirated between successive liquid samples, and air is aspirated between the sample and wash segments. The volumes of successive liquid samples intended for analysis are thus separated by at least a wash liquid segment and two occluding air segments. Each air segment serves to scrub the interior surface wall to remove sample residue therefrom, whereas the following wash liquid segment entrains the dislodged residue. The introduction of the wash liquid segment between successive liquid samples is achieved by providing a wash liquid reservoir into which a sample probe is immersed between immersion thereof in successive liquid samples.

One object of the invention is to further reduce contamination between successive liquid samples introduced into automatic analysis apparatus. In accordance with one feature of the present invention, there is provided a sample supply apparatus for a continuous flow analysis system, comprising an off-take tube which extends in use axially into another tube, of larger diameter than the off-take tube, through which a main stream of liquid segmented by segments of immiscible fluid is passed, the arrangement being such that an axial portion of such a main segmented stream is carried into the off-take tube, wherein said portion is of smaller volume than the main stream, but is segmented by said fluid at intervals substantially the same as the main stream.

In accordance with another feature of the present invention, there is provided a sample supply apparatus comprising as aspirating off-take tube, a carrier for a plurality of liquid sample receptacles, a wash liquid supply device positively located relative to said carrier, said device comprising a tube along which wash liquid segmented by immiscible fluid, such as gas bubbles is passed as a continuous main stream, and means for moving said probe into and out of said sample receptacles and substantially axially into and out of said tube between successive movements into said sample receptacles, to withdraw an axial portion of the segmented wash stream into the off-take tube, said portion being segmented in a manner similar to but having a volume smaller than said main wash stream.

In accordance with a further feature of the invention, there is provided a method of obtaining for a continuous-flow analysis system a stream of liquid segmented by an immiscible fluid, said method comprising the steps of passing a main stream of the liquid segmented by segments of the immiscible through a first tube, locating axially of the first tube an off-take tube having a diameter less than that of the first tube, and withdrawing along the off-take tube an axial portion of the segmented stream, the portion having a volume smaller than the main stream volume but being segmented by the fluid at intervals substantially the same as the main stream.

A sample supply apparatus in accordance with the invention for an automatic analysis system will now be described, by way of example, with reference to the accompanying drawings, in which.

Figure 1:
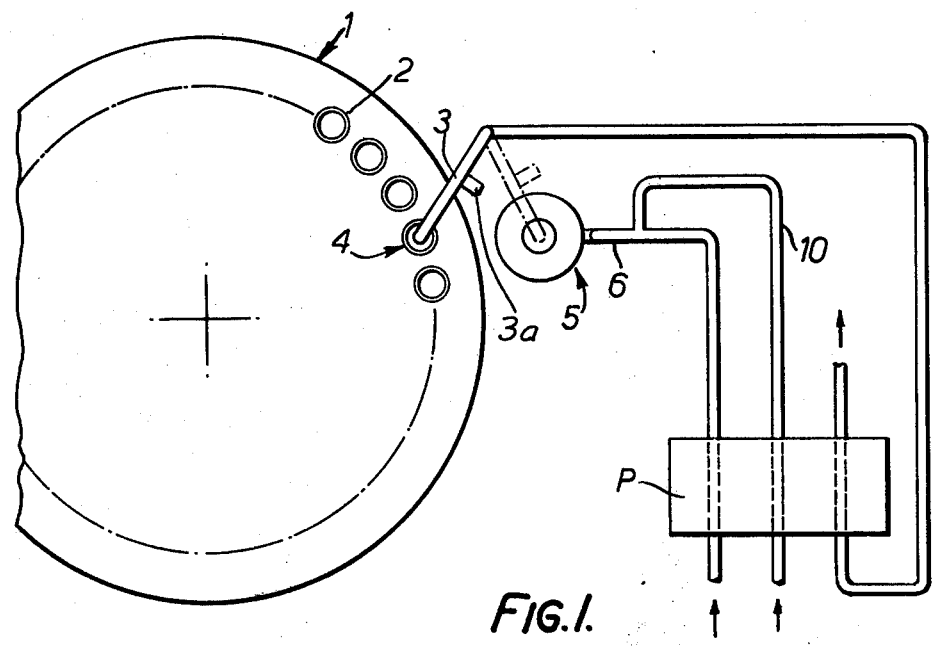
FIG. 1 is a diagrammatic plan view of part of the apparatus.

The supply apparatus is generally similar to the sample supply device described in de Jong U.S. Pat. No. 3,134,263, but with the wash receptacle of said sample supply device being replaced by the wash liquid supply device illustrated in FIG. 2.

Briefly, the illustrated sample supply apparatus 1 comprises a carrier in the form of a turntable which supports a plurality of removable sample cups 2. The turntable is intermittently turned by a suitable drive mechanism (not shown) to present the cups successively to a sample probe or take-off device 3 at a sample supply station 4. The probe is mounted to one side of the cups 2 for lateral movement by a power-operated arm 3a between a position above the cups 2 and a position above the wash liquid supply device 5 and for up and down movement into and out of the cup at the sample supply station 4 and into and out of the supply device 5.

The wash liquid supply device 5 comprises a conduit 6 having a U-shaped portion 7, one arm 7A of which has an open frustoconical end 8 and is supported in an outer casing 9.

Wash liquid W including a wetting agent is pumped along the conduit 6, for example, by means of a peristaltic pump P, and air A or other gas is periodically introduced into the wash liquid through a conduit 10 by pump P so that a stream of wash liquid segmented by air passes through the U-shaped portion 7 while maintaining bubble integrity. The periodic introduction of air could for example, be effected using a mechanism such as described in U.S. Pat. No. 3,654,959.

Figure 2:
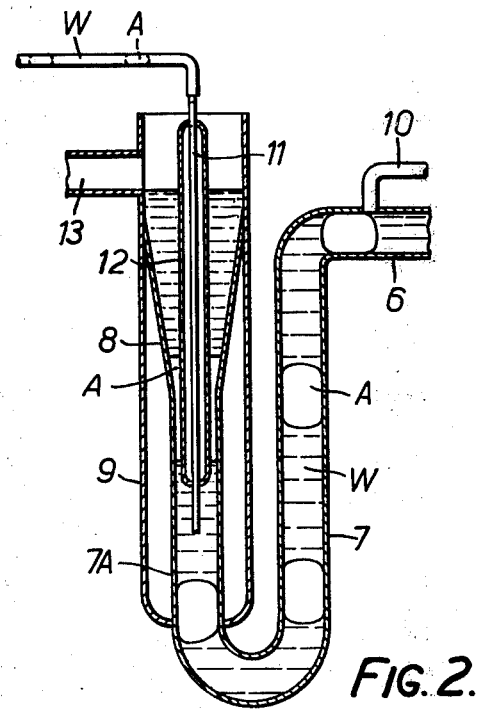
FIG. 2 is an enlarged diagrammatic axial section of a wash liquid supply device of the apparatus.

The probe 3 has a tube 11 which is arranged to extend axially into the arm 7A of the conduit 6 and an outer support 12 which, when the probe is inserted in the conduit 6 as illustrated in FIG. 2, partially occludes the conduit above the tip of the probe to restrict the flow of wash liquid through the conduit 6 beyond the probe tip.

In operation, the probe 3, which is connected to the peristaltic pump P as shown, is lowered into a sample cup 2 at the sample station to aspirate sample liquid from the cup. After a predetermined time, the probe is lifted out of the cup 2 and moved across to a position above the wash liquid supply device 5 and then axially into the arm 7A of the device, the funnel 8 ensuring that the probe is guided axially into the arm 7A. During the time the probe moves from the sample to the wash liquid, air is aspirated into the probe. The probe, while at rest in the arm 7A with clearance therebetween, aspirates an axial portion of the segmented wash liquid stream for a predetermined time and is lifted back into the next successive sample cup which has been indexed to the sample supply station. Successive samples are thus separated by a wash liquid stream segmented by a selected number of occluding air bubbles and are passed to the analytical part of the system. The number of air bubbles in the separating wash liquid stream is controllable and is a function of the rate at which the air segments are introduced into the conduit 6 and the immersion time of the probe in the arm 7A.

The wash liquid stream that is not aspirated into the probe flows beyond the probe tip into the funnel 8 where the air separates from the wash liquid, the latter flowing out through an overflow 13 to waste.

The peristaltic pump may cause pulses in the segmented stream passing through the portion 7 of conduit 6 with the result that the velocity of the stream may be momentarily reduced at predetermined intervals of time. Preferably, the air is introduced into the stream simultaneously with the pulses occuring to reduce the effect of the pulses. In addition the distance between the junction of conduits 6 and 10 and the probe tip when inserted in the arm 7A is preferably arranged so that pulsing of the wash liquid flow does not cause a change in the flow rate when an air bubble is coincident with the tip, which would lead to irregular sizes of aspirated air bubbles.

For some applications irregularities which may be caused by the insertion or withdrawal of the probe in the arm 7A are not critical. However, the speed of the probe may be related to the speed of the air bubbles along arm 7A and the probe may be raised at a time when the tip is immersed in a wash liquid segment to help maintain constant air bubble size.

The restriction beyond the probe tip caused in the above described apparatus by the outer support 12 of the probe 3 is sufficient to ensure that the integrity of the air bubbles drawn into the probe 3 is maintained and that the air bubbles in the arm 7A do not simply break up in the region of the probe tip.

The above described apparatus eliminates or reduces carryover from one sample to the successive sample using a simple and relatively inexpensive wash liquid supply device for segmenting the wash liquid stream. It is particularly useful in "yes/no" test such as complement fixation tests, anti-body screening tests and automated reagin tests.

While the presently preferred embodiment of the fluid supply apparatus has been illustrated and described, it will be apparent, especially to those versed in the art, that the invention may take other forms and is susceptible to changes in details without departing from the principles of the invention.

What is claimed is:

1. Fluid supply apparatus for a continuous-flow system, comprising: a conduit element, means flowing a liquid stream segmented by segments of an immiscible fluid along said conduit element, an off-take tube element having an inlet portion movable to first and second positions, means to move said inlet portion to said positions, said inlet portion in said first position being in fluid-flow communication with said stream and disposed within said conduit element, and aspirating means connected to said tube element and removing a portion of successive segments of said liquid and immiscible fluid, in turn, from said stream while said tube element is in said first position, said inlet portion being removed from said fluid-flow communication while in said second position.

2. Apparatus as defined in claim 1, wherein: said tube inlet portion extends axially into said conduit element in said first position and is of a cross-sectional dimension which does not occlude said conduit element.

3. Apparatus as defined in claim 1, wherein: said tube inlet portion in said second position is in fluid-flow communication with a different fluid, and said aspirating means aspirates said different fluid through said tube element.

4. Apparatus as defined in claim 2, wherein one of said elements has a protuberance restricting the flow in said conduit element and spaced a distance downstream from said tube inlet portion in said first position of said inlet portion, said segmenting fluid being a gas.

5. Apparatus as defined in claim 2, wherein said conduit element comprises an open funnel-shaped end guiding said tube element thereinto and through which said tube inlet portion extends.

6. Sample supply apparatus, comprising: an aspirating off-take tube having an inlet portion; a carrier for a plurality of upwardly opening receptacles each containing a liquid sample; a wash liquid supply device laterally of said carrier, said supply device comprising a conduit of internal cross-sectional dimension to axially receive said tube inlet portion, said conduit having an open end, said supply device further comprising means flowing liquid segmented by gas segments along said conduit towards said conduit end; and means including aspirating means moving said tube inlet portion into and out of successive ones of said receptacles and, alternately, into and out of said conduit end between successive movement into said receptacles to aspirate a number of successive liquid and gas segments, in turn, flowing along said conduit intermediate successive aspirations of said liquid samples.

7. Fluid supply apparatus, comprising: a conduit having an outlet, a tube having an inlet portion, means flowing a stream of liquid segmented by immiscible fluid segments along said conduit toward said outlet, means intermittently moving said tube to axially position said inlet portion within said conduit and in fluid-flow communication with said stream, and aspirating means connected to said tube to aspirate a portion of said liquid segments and immiscible fluid segments, in turn, when said inlet portion is positioned within said conduit.

8. A method of obtaining for a continuous flow analysis system a stream of successive liquid segments separated by immiscible fluid segments, comprising the steps of:

flowing a stream of liquid separated by immiscible fluid segments along a conduit toward an outlet thereof;

intermittently positioning an inlet portion of a tube within said conduit and in fluid-flow communication with said stream; and aspirating through said tube a portion of said successive liquid and immiscible fluid segments, in turn, when said inlet portion is positioned within said conduit.

9. A method as defined in claim 8, further including positioning said tube inlet portion axially within said conduit, and flowing the unaspirated portion of said stream along said conduit and beyond said inlet portion.

10. A method as defined in claim 8, further including positioning said tube inlet portion in a second position and in fluid-flow communication with a different source of fluid, and aspirating said fluid from said different source through said tube while said inlet portion is in said second position.

11. A method as defined in claim 8, further including positioning said tube inlet portion in said position to extend into said conduit with clearance, flowing the unaspirated portion of said stream beyond said inlet portion, and partially restricting the flow of said stream in said conduit at a location spaced downstream from said inlet portion.

12. A method as defined in claim 11, further including maintaining said inlet portion immersed in a liquid segment of said stream as said inlet portion is removed from said conduit.

13. A method as defined in claim 11, further including intermittently introducing said gas segments into liquid continuously flowing along said conduit to form said stream, and maintaining said tube inlet portion immersed in a liquid segment when a gas segment is introduced into said liquid.

* * * * *